(12) United States Patent
DeLuca et al.

(10) Patent No.: US 8,349,818 B2
(45) Date of Patent: Jan. 8, 2013

(54) METHOD OF PREVENTING TYPE 1 DIABETES

(75) Inventors: Hector F. DeLuca, Deerfield, WI (US); Jamie Nehring, Sauk City, WI (US); Ehren N. Rudolph, Minneapolis, MN (US); Lori Plum, Arena, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 3 days.

(21) Appl. No.: 12/909,253

(22) Filed: Oct. 21, 2010

(65) Prior Publication Data
US 2011/0124609 A1 May 26, 2011

Related U.S. Application Data

(60) Provisional application No. 61/253,665, filed on Oct. 21, 2009.

(51) Int. Cl.
*A61K 31/59* (2006.01)
(52) U.S. Cl. ...................................................... 514/167
(58) Field of Classification Search .................. 514/167
See application file for complete search history.

(56) References Cited

U.S. PATENT DOCUMENTS

| | | | |
|---|---|---|---|
| 4,666,634 A | 5/1987 | Miyamoto et al. | |
| 5,086,191 A | 2/1992 | DeLuca et al. | |
| 5,536,713 A | 7/1996 | DeLuca et al. | |
| 5,665,387 A | 9/1997 | Mathieu et al. | |
| 5,843,928 A | 12/1998 | DeLuca et al. | |
| 5,945,410 A | 8/1999 | DeLuca et al. | |
| 6,277,837 B1 | 8/2001 | DeLuca, Jr. et al. | |
| 7,094,774 B2 | 8/2006 | DeLuca et al. | |
| 7,713,951 B2 * | 5/2010 | DeLuca et al. | 514/167 |
| 2006/0003973 A1 | 1/2006 | DeLuca et al. | |
| 2006/0079490 A1 | 4/2006 | DeLuca et al. | |
| 2006/0189576 A1 | 8/2006 | Bouillon et al. | |

FOREIGN PATENT DOCUMENTS

WO  2005011706 A1  2/2005

OTHER PUBLICATIONS

DeLuca, et al., Selective Analogs of 1alpha,25-dihydroxyvitamin D3 for the Study of Specific Functions of Vitamin D, Journal of Steroid Biochemistry & Molecular Biology, 2007, 103:263-268.
Makishima, et al., Targeting the Vitamin D Receptor: Advances in Drug Discovery, Expert Opin. Ther. Patents, 2005, 15(9):1133-1145.
Vanhooke, et al., New Analogs of 2-methylene-19-nor-(20S)-1,25-dihydroxyvitamin D3 with Conformationally Restricted Side Chains: Evaluation of Biological Activity and Structural Determination of VDR-Bound Conformations, Archives of Biochemistry and Biophysics, 2007, 460:161-165.
Williams, et al., 2-Methylene-19-nor-20(S)-1alpha-hydroxy-bishomopregnacalciferol [20(S)-2MbisP], An Analog of Vitamin D3 [1,25(OH)2D3], Does Not Stimulate Intestinal Phosphate Absorption at Levels Previously Shown to Suppress Parathyroid Hormone, Steroids, 2008, 73:1277-1284.
PCT International Search Report and Written Opinion, Application No. PCT/US2010/053550, May 19, 2011.
DeLuca, 2004, Am. J. Clin. Nutr. 80 (suppl):1689S-1696S.
Eisenbarth, 1986, New Engl. J. Med. 314:1360-1368.
Foster, 1983, Harrison's Principles of Internal Medicine Tenth Edition, Chap. 114, pp. 661-679, McGraw-Hill Book Company, New York.
Jones, et al., 1998, Physiol. Rev. 78:1193-1231.
Miyamoto, et al., 1993, Chem. Pharm. Bull. 41:1111-1113.
Nakhooda, et al., 1978, Diabetologia 14:199-207.
Nishii, et al., 1993, Osteoporosis Int. Suppl. 1:S190-193.
Okano, et al., 1989, Biochem. Biophys. Res. Commun. 163:1444-1449.
Ostrem, et al., 1987, Proc. Natl. Acad. Sci. USA 84:2610-2614.
Perlman, et al., 1990, Tetrahedron Lett. 31:1823-1824.
Perlman, et al., 1991, Tetrahedron Lett. 32:7663-7666.
Posner, et al., 1994, J. Org. Chem. 59:7855-7861.
Posner, et al., 1995, J. Org. Chem. 60:4617-4628.
Prochazka, et al., 1987, Science 237:286-289.
Smith, et al., 1987, J. Nutr. 117:857-865.
Suda, et al., 1970, J. Nutr. 100:1049-1052.
Tochino, et al., 1987, Crit. Rev. Immunol. 8:49-81.
Zella, et al., 2003, Arch. Biochem. Biophys. 417:77-80.
U.S. Appl. No. 09/616,164, filed Jul. 14, 2000.

* cited by examiner

*Primary Examiner* — Rei-tsang Shiao
(74) *Attorney, Agent, or Firm* — Quarles & Brady LLP

(57) ABSTRACT

The invention relates to novel methods of using 2α-methyl-19-nor-20(S)-1α,25-dihydroxyvitamin $D_3$ or 2-methylene-19-nor-20(S)-1,25-dihydroxyvitamin $D_3$ to prevent Type 1 diabetes in a subject at risk of developing Type 1 diabetes without causing hypercalcemia in the subject.

6 Claims, 6 Drawing Sheets

METHOD OF PREVENTING TYPE 1 DIABETES

CROSS REFERENCE TO RELATED APPLICATIONS

Figure 1:
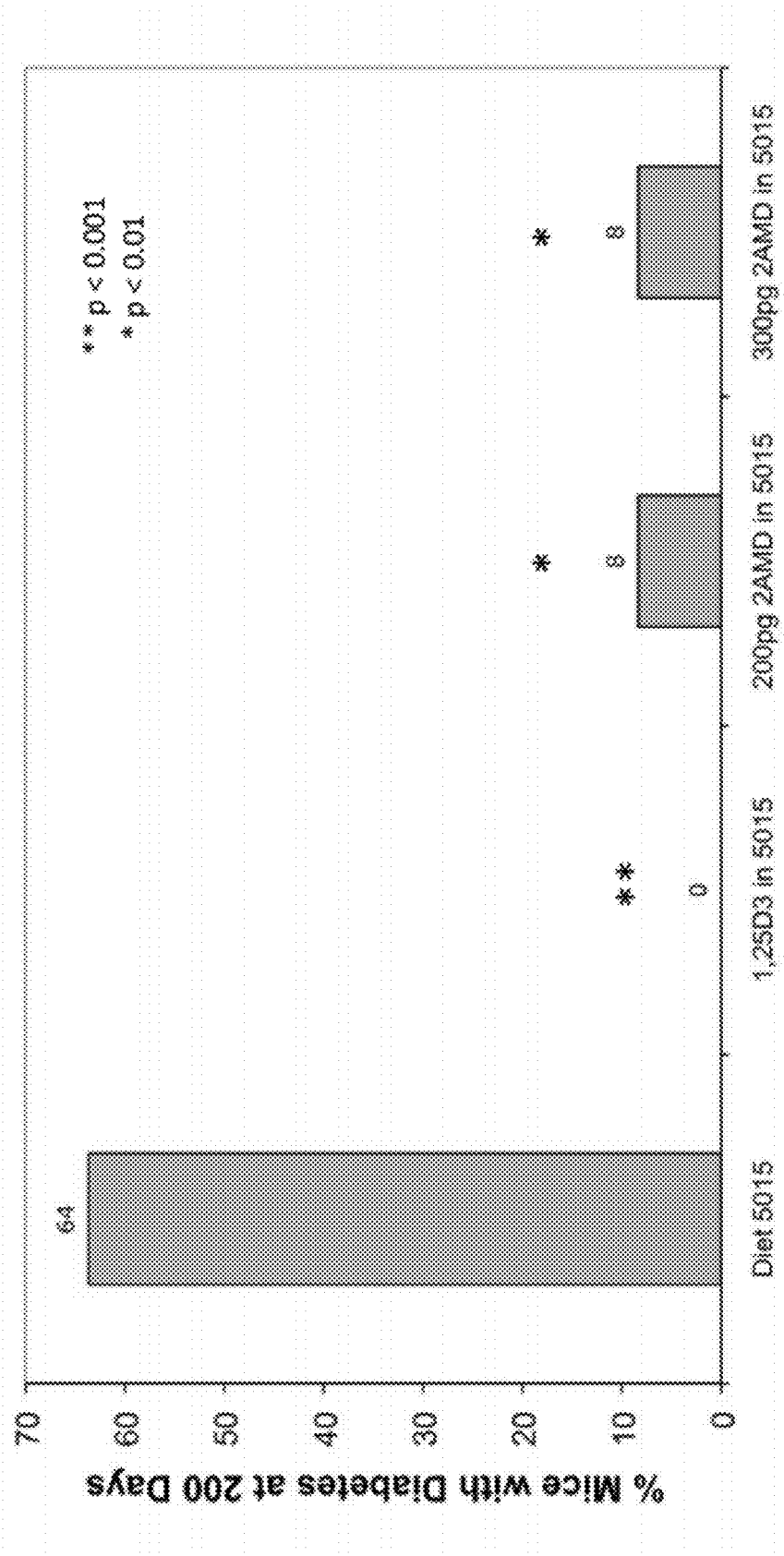

This application claims priority to U.S. Provisional Application No. 61/253,665, filed Oct. 21, 2010, which is hereby incorporated herein by reference for all purposes.

STATEMENT CONCERNING GOVERNMENT INTEREST

Not applicable.

FIELD OF THE INVENTION

This invention relates to vitamin D compounds useful in preventing Type 1 Diabetes and also discloses technology related to that disclosed in U.S. Published Patent Application Nos. US 2006/0079490 (pending) and 2006/0003973 (abandoned), which are hereby incorporated herein by reference for all purposes.

BACKGROUND OF THE INVENTION

Diabetes mellitus is a metabolic disorder that occurs in approximately four percent of humans. There are two types of diabetes; the non-insulin-dependent or "maturity onset" form (Type 2) and the insulin-dependent or "juvenile onset" form (Type 1). Clinically, the majority of Type 2 diabetics are obese, with manifestations of clinical symptoms of the disease usually appearing in patients over age 40. In contrast, Type 1 diabetics are usually not over-weight relative to their age and height and typically exhibit rapid onset of the disease at an early age, often before age 30.

One-third of diabetes patients suffer from Type 1 diabetes (Foster et al., *Harrison's Principles of Internal Medicine*, Chap. 114, pp. 661-678, 10th Ed., McGraw-Hill, New York). Type 1 diabetes is an autoimmune disease wherein a state of hyperglycemia results from the T-cell mediated destruction of insulin-secreting b-cells in the pancreatic Islets of Langerhans (Eisenbarth et al., 1986, *New Engl. J. Med.* 314: 1360-1368). The disease manifests itself as a series of hormone-induced metabolic abnormalities which eventually lead to serious, long-term and debilitating complications involving several organ systems including the eyes, kidneys, nerves, and blood vessels. Pathologically, the disease is characterized by lesions of the basement membranes, demonstrable under electron microscopy.

Type 1 diabetics characteristically show very low or immeasurable plasma insulin with elevated glucagon. Regardless of what the exact etiology is, most Type 1 patients have circulating antibodies directed against their own pancreatic cells including antibodies to insulin, to the islet of Langerhans cell cytoplasm and to the enzyme glutamic acid decarboxylase. An immune response specifically directed against beta cells (insulin producing cells) leads to Type 1 diabetes.

Current therapeutic regimens for Type 1 diabetes include modifications to the diet to minimize hyperglycemia resulting from the lack of natural insulin, which in turn, is the result of damaged beta cells. Diet is also modified with regard to insulin administration to counter the hypoglycemic effects of the hormone. Whatever the form of treatment, parenteral administration of insulin is required for all Type 1 diabetics, hence the term "insulin-dependent" diabetes.

Because Type 1 diabetes usually manifests itself in adolescents and because the subcutaneous delivery of insulin requires strict self-regimentation, compliance is often a serious problem. For the clinician, it is difficult to precisely regulate the amounts of insulin needed at any given time of the patient's day. Furthermore, it is all but impossible to regulate blood glucose levels in diabetic patients with parenteral insulin to the extent to which blood glucose is regulated in normal individuals.

Thus, in the early stages of treatment of Type 1 diabetes, patients often become either hyperglycemic or hypoglycemic because the exact timing of the insulin injections and levels of insulin needed are not known. As treatment progresses the clinician and, more importantly, the patient adjusts to the daily routine, but there is always the risk of ketoacidosis or hypoglycemia.

The pathogenesis of Type 1 diabetes is not fully understood, although various animal models are available for its study. These include the BB mouse (Nakbookda et al., 1978, *Diabetologic* 14: 199-207,) and the NOD (non-obese diabetic) mouse in which diabetes develops spontaneously (Prochazka et al., 1987, *Science* 237:286). These mice, especially females, are genetically susceptible to diabetes. Similar to the human condition, the NOD mouse exhibits hyperglycemia, polyuria, polydipsia, glucosuria, insulitis and a dependence on exogenous insulin to sustain life (Tochino et al., 1987, *Crit. Rev. Immunol.* 8:49-81). Such characteristics have made the NOD mouse an excellent and widely accepted murine model of human Type 1 diabetes.

Vitamin D is a known and potent regulator of calcium and phosphorous metabolism. The biologically active form of Vitamin D, $1\alpha,25$-dihydroxyvitamin $D_3$, and its analog in ergocalciferol series, $1\alpha,25$-dihydroxyvitamin $D_2$, are highly effective regulators of calcium homeostasis in animals and humans (Ostrem et al., 1987, *Proc. Natl. Acad. Sci. USA* 84:2610). Many structural analogs of these metabolites have been prepared and tested including $1\alpha$-hydroxyvitamin $D_3$ and $1\alpha$-hydroxyvitamin $D_2$, each having various homologated side chains and fluorinated analogs thereof. Some compounds exhibited separated cell differentiation and calcium regulation activity. The physiology and molecular actions of vitamin D and its various analogs and metabolites are discussed in Jones et al., 1998, *Physiol. Rev.* 78:1193-1231 and DeLuca, 2004, *Am J Clin Nutr* 80 (suppl):16895-16965, which are hereby incorporated herein by reference.

Another class of vitamin D analogs, 19-nor-vitamin D compounds, are characterized by the replacement of the A-ring exocyclic methylene group (carbon 19) by two hydrogen atoms. Biological testing of the 19-nor-analogs (e.g., $1\alpha,25$-dihydroxy-19-nor-vitamin $D_3$) demonstrated a selective activity profile having high potency for inducing cellular differentiation as well as very low calcium mobilizing activity. Two synthetic methods have been reported (Perlman et al., 1990, *Tetrahedron Lett.* 31:1823; Perlman et al., 1991, *Tetrahedron Lett.* 32:7663, and DeLuca et al., U.S. Pat. No. 5,086, 191).

U.S. Pat. No. 4,666,634 to Miyamoto et al. describes $2\beta$-hydroxy and alkoxy analogs of $1\alpha,25$-dihydroxyvitamin $D_3$ as potential drugs for osteoporosis and as antitumor agents. (See also Okano et al., 1989, *Biochem. Biophys. Res. Commun.* 163:1444). Other 2-substituted hydroxyalkyl and fluoroalkyl groups A-ring analogs of $1\alpha,25$-dihydroxyvitamin $D_3$ have also been reported (Miyamoto et al., 1993, *Chem. Pharm. Bull.* 41:1111; Nishii et al., 1993, *Osteoporosis Int. Suppl.* 1:190; Posner et al., 1994, *J. Org. Chem.* 59:7855 and Posner et al., 1995, *J. Org. Chem.* 60:4617).

2-substituted analogs of 1α,25-dihydroxy-19-nor-vitamin D$_3$ have also been synthesized and reported, which are compounds substituted at 2-position with hydroxy or alkoxy groups (DeLuca et al., U.S. Pat. No. 5,536,713). Binding sites in vitamin D receptors can accommodate different substituents at C-2 in these 19-nor vitamin D analogs.

SUMMARY OF THE INVENTION

The present invention provides novel methods of preventing Type 1 diabetes in a subject at risk of developing Type 1 diabetes. Specifically, the method comprises administering to the subject a therapeutically effective amount of 2α-methyl-19-nor-20(S)-1α,25-dihydroxyvitamin D$_3$ (2AMD) or 2-methylene-19-nor-20(S)-1,25-dihydroxyvitamin D$_3$ (2MD), wherein Type 1 diabetes is prevented from developing in the subject without inducing hypercalcemia in the subject.

In an exemplary embodiment, the 2α-methyl-19-nor-20(S)-1α,25-dihydroxyvitamin D$_3$ or 2-methylene-19-nor-20(S)-1,25-dihydroxyvitamin D$_3$ is formulated in an oral, topical, transdermal, parenteral, injection or infusion dosage form.

In another exemplary embodiment, the therapeutically effective amount of 2AMD ranges from about 100 pg/kg body weight to about 500 pg/kg body weight per day, while the therapeutically effective amount of 2MD ranges from about 0.1 ng/kg body weight per day to about 5 ng/kg body weight per day.

Other features of the present invention will become apparent after review of the specification, claims and drawings.

BRIEF DESCRIPTION OF DRAWINGS OF THE EXEMPLARY EMBODIMENTS

FIG. 1 is a bar graph showing a comparison between the diabetes incidence in NOD mice fed diet 5015 at 200 days treated with 50 ng 1α,25-dihydroxy-vitamin D$_3$ (also referred to herein as 1,25D$_3$ and 1,25(OH)$_2$D$_3$), 200 pg 2α-methyl-19-nor-20(S)-1α,25-dihydroxyvitamin D$_3$ (referred to herein as 2AMD), 300 pg 2AMD, as well as no treatment, whereby the data demonstrate that treatment with 2AMD caused a statistically significant reduced incidence of diabetes. Female NOD mice were fed ad libitum on the indicated diets for 200 days. There were 24 mice per group and the daily dose of analog provided in the diet is shown.

Figure 2:
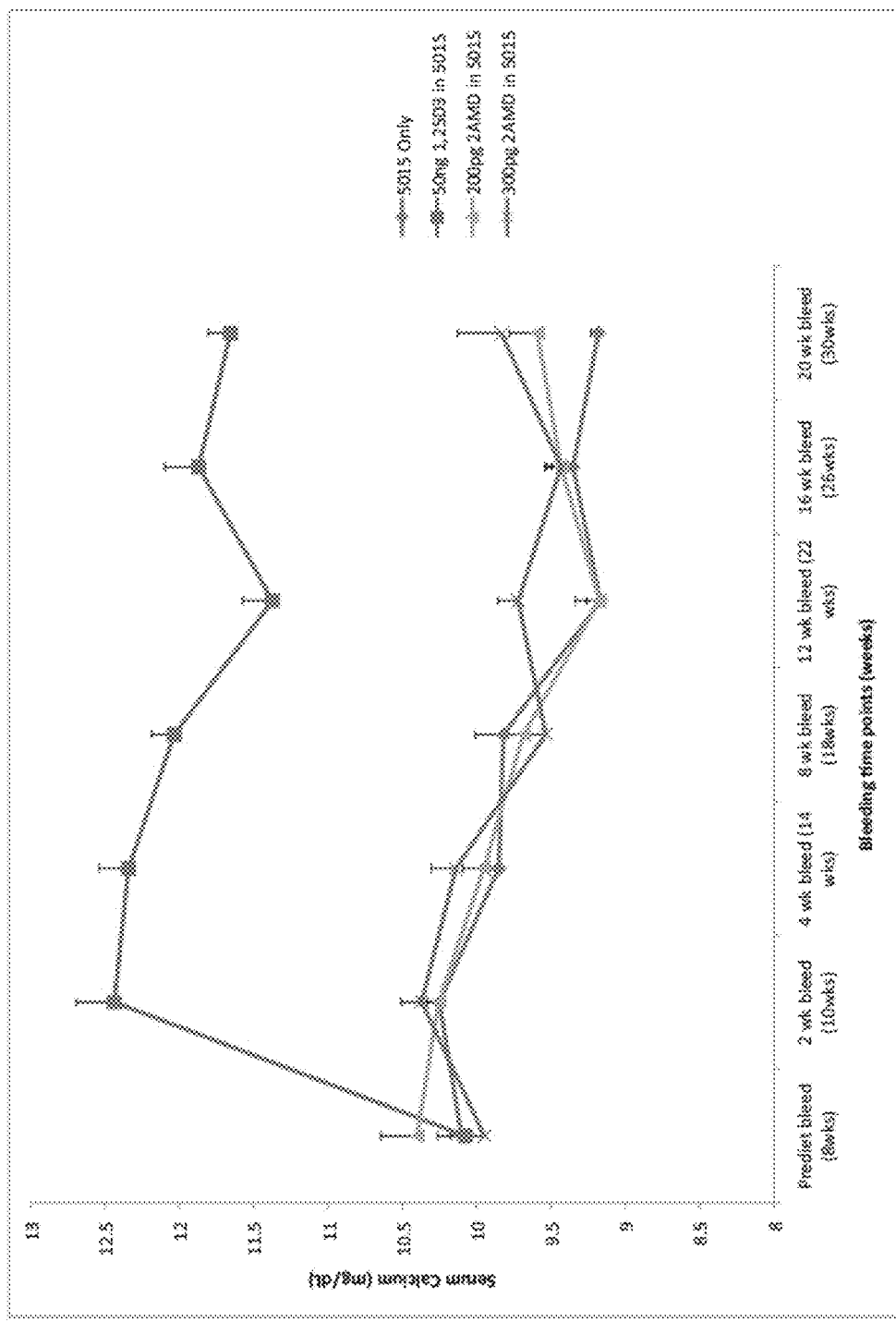

FIG. 2 is a graph showing a comparison of serum calcium levels in the NOD mice described in FIG. 1 over 30 weeks as treated with 50 ng 1,25D$_3$, 200 pg 2AMD and 300 pg 2AMD, whereby the data demonstrate that treatment with 2AMD caused no statistically significant increase in serum calcium.

Figure 3:
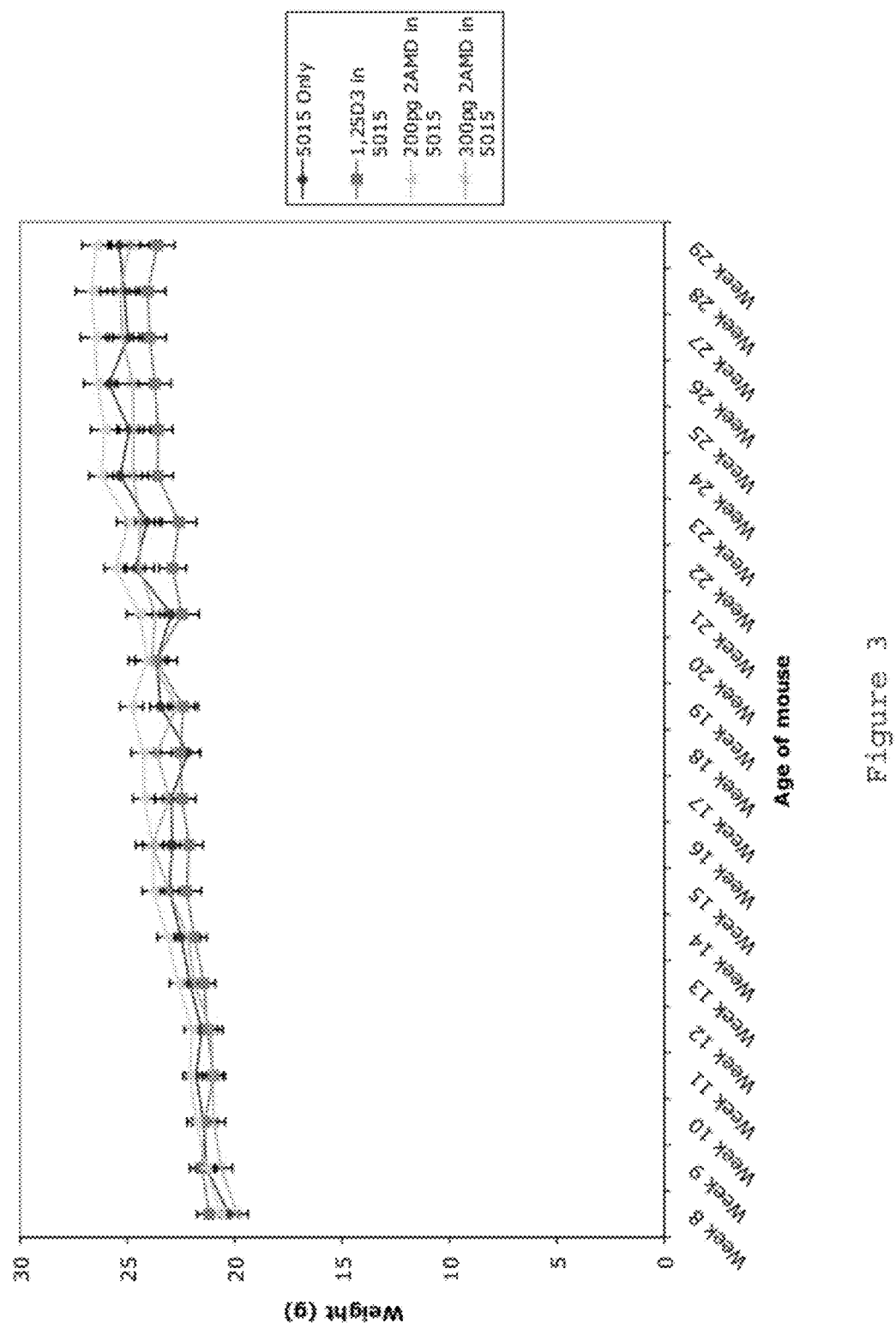

FIG. 3 is a graph showing a comparison of animal weight over 200 days in the mice described in FIG. 1 as treated with 50 ng 1,25D$_3$, 200 pg 2AMD and 300 pg 2AMD, whereby the data demonstrate that treatment with 2AMD caused no statistically significant change in body weight.

Figure 4:
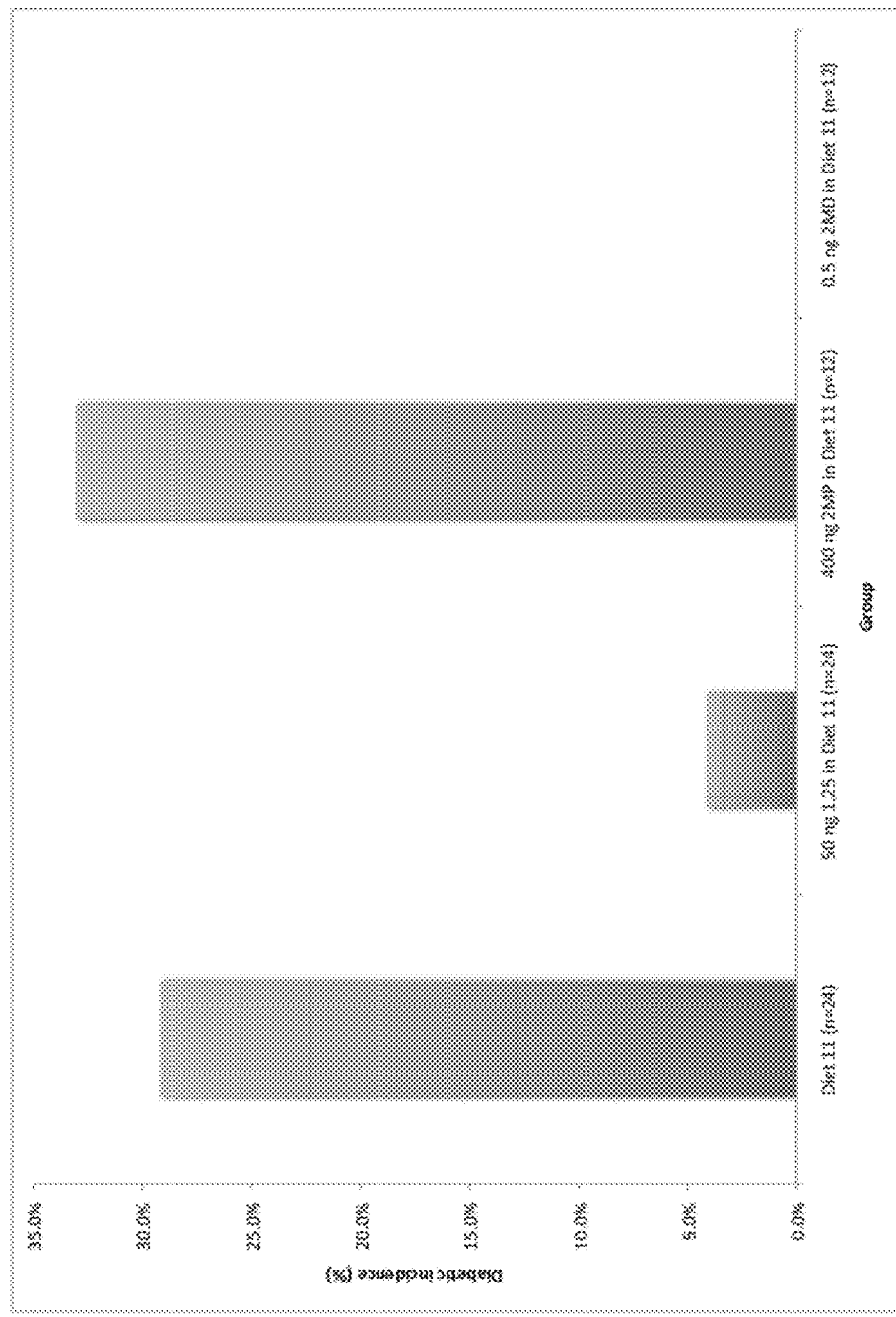

FIG. 4 is a bar graph showing a comparison between the diabetes incidence in NOD mice fed diet 11 with and without the indicated daily dose of vitamin D analogs for 200 days at 200 days treated with 50 ng 1α,25-dihydroxy-vitamin D$_3$ (also referred to herein as 1,25D$_3$ and 1,25(OH)$_2$D$_3$), 400 ng 1α-hydroxy-2-methylene-19-nor-homopregnacalciferol (referred to herein as 2MP) and 0.5 ng 2-methylene-19-nor-20(S)-1,25-dihydroxyvitamin D$_3$ (referred to herein as 2MD) as well as no treatment, whereby the data demonstrate that treatment with 2MD caused a statistically significant reduced incidence of diabetes. There were 24 female mice per group.

Figure 5:
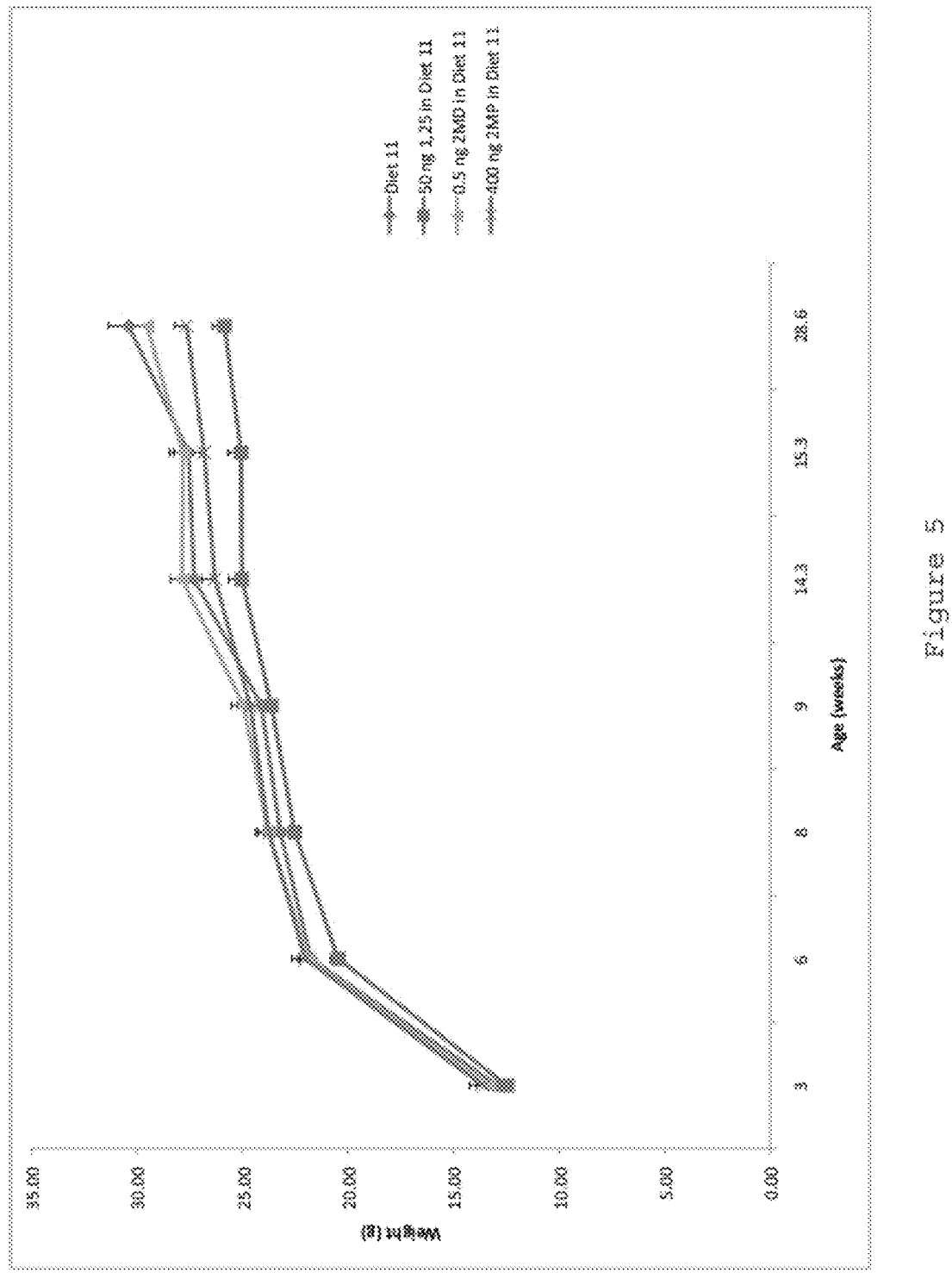

FIG. 5 is a graph showing a comparison of animal weight over 200 days of the mice described in FIG. 4 as treated with 50 ng 1,25D$_3$, 400 ng 2MP and 0.5 ng 2MD, whereby the data demonstrate that treatment with 2MD caused no statistically significant change in body weight.

Figure 6:
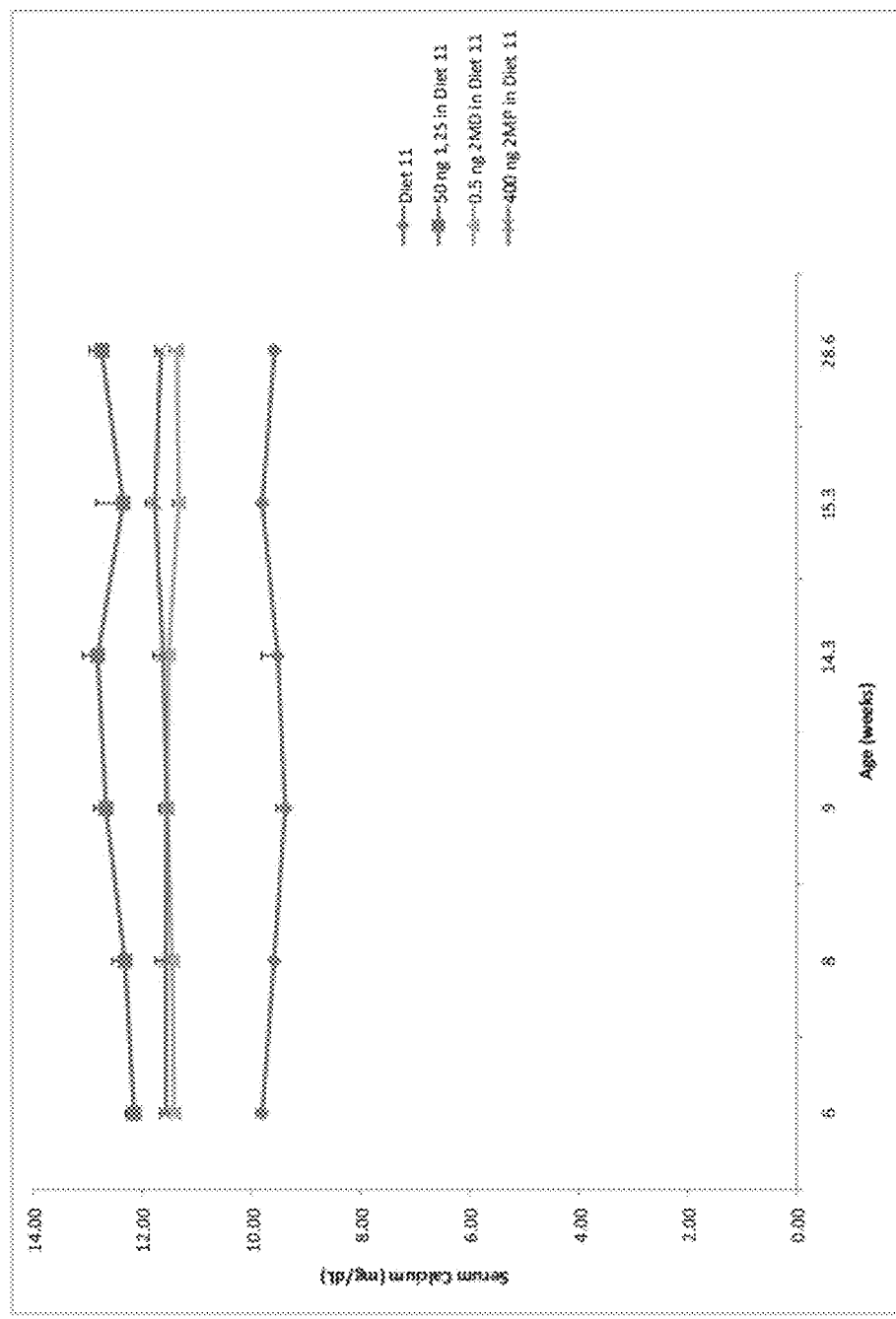

FIG. 6 is a graph showing a comparison of serum calcium levels in the NOD mice described in FIG. 4 over 30 weeks as treated with 50 ng 1,25D$_3$, 400 ng 2MP and 0.5 ng 2MD, whereby the data demonstrate that treatment with 2MD caused no statistically significant increase in serum calcium.

DETAILED DESCRIPTION OF THE EXEMPLARY EMBODIMENTS

I. In General

In the specification and in the claims, the terms "including" and "comprising" are open-ended terms and should be interpreted to mean "including, but not limited to . . . ." These terms encompass the more restrictive terms "consisting essentially of" and "consisting of."

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention

The present invention provides novel methods of preventing Type 1 diabetes in a subject at risk of developing Type 1 diabetes by administering to the subject a therapeutically effective amount of 2α-methyl-19-nor-20(S)-1,25-dihydroxyvitamin D$_3$ (2AMD) or 2-methylene-19-nor-20(S)-1,25-dihydroxyvitamin D$_3$ (2MD) to prevent Type 1 diabetes without inducing hypercalcemia in the subject. Specifically, the present invention demonstrates that 2α-methyl-19-nor-20(S)-1,25-dihydroxyvitamin D$_3$ (2AMD) and 2-methylene-19-nor-20(S)-1,25-dihydroxyvitamin D$_3$ (2MD) are able to prevent a subject from developing Type 1 diabetes without raising serum calcium (to any statistically significant degree).

Previously, this laboratory demonstrated that 50 micrograms per day of 1,25-(OH)$_2$D$_3$ will completely prevent Type 1 diabetes in the NOD mouse (Zella et al., 2003, *Arch. Biochem. Biophys.* 417:77-80). However, severe hypercalcemia always accompanied this activity. Hypercalcemia (increased levels of calcium in the blood) can result in serious physical problems, including death. Clearly, the use of 1,25-(OH)$_2$D$_3$ is obviously not possible because of the resultant hypercalcemia. Accordingly, a need exists for compounds that will prevent Type 1 Diabetes but that will not raise serum calcium.

An analog characterized by the presence of a methyl substituent at C-2 has been synthesized and tested. Such analogs are characterized by the unnatural configuration of the methyl group at C-20 (e.g., 2α-methyl-19-nor-20(S)-1α,25-dihydroxyvitamin D$_3$). The relatively small methyl group or methylene at C-2 may not interfere with binding to the vitamin D receptor. Molecular mechanics studies performed on the model 1α-hydroxy-2-methylene-19-nor-vitamins indicate that such molecular modification does not substantially change the conformation of the cyclohexanediol ring A.

Introducing the 2-methylene group into 19-nor-vitamin D carbon skeleton changes the character of its 1α- and 3β-A-ring hydroxyls. Both hydroxyls are allylic to the exocyclic methylene group similar to the 1α-hydroxyl group (crucial for biological activity) in the molecule of the natural hormone, 1α,25-(OH)$_2$D$_3$.

In one embodiment, the invention provides a method of preventing Type 1 diabetes in a subject at risk of developing Type 1 diabetes comprising administering to the subject a therapeutically effective amount of 2α-methyl-19-nor-20(S)-1α,25-dihydroxyvitamin D$_3$ (2AMD) having the structure:

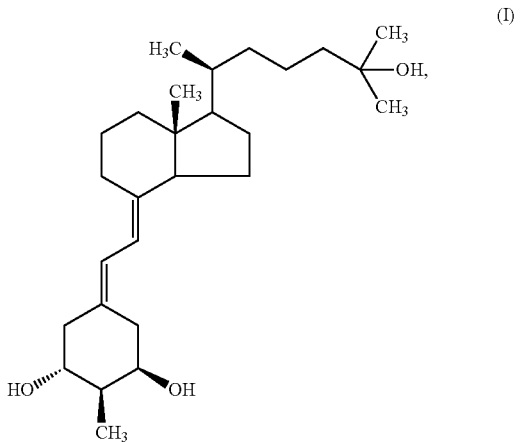

(I)

without increasing the serum calcium levels of the subject.

In one embodiment, the method of the present invention prevents a subject from developing Type 1 diabetes by preventing destruction of the islet cells.

The overall synthesis of compound I is further illustrated and described in U.S. Pat. No. 5,945,410 entitled "2-Alkyl-19-Nor-Vitamin D Compounds," which is incorporated herein by reference.

In another embodiment, the invention provides a method of preventing Type 1 diabetes in a subject at risk of developing Type 1 diabetes comprising administering to the subject a therapeutically effective amount of 2-methylene-19-nor-20 (S)-1,25-dihydroxyvitamin D$_3$ (2MD) having the structure (II):

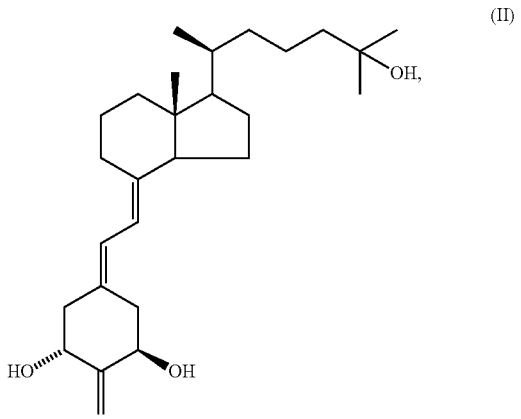 [SMILES: C=C1[C@H](O)CC(=C/C=C2\CCC[C@@]3(C)C2CCC3[C@@H](C)CCCC(C)(C)O)C[C@H]1O]

(II)

without inducing hypercalcemia in the subject.

The overall synthesis of compound II is illustrated and described more completely in U.S. Pat. No. 5,843,928, issued Dec. 1, 1998, and entitled "2-Alkylidene-19-Nor-Vitamin D Compounds" the specification of which is specifically incorporated herein by reference. The biological activity of 2MD is reported in U.S. patent application Ser. No. 09/616,164, filed Jul. 14, 2000, the specification of which is also specifically incorporated herein by reference.

In one embodiment, the method of the present invention prevents a subject from developing Type 1 diabetes by preventing the destruction of the islet cells.

By "preventing" we mean a forestalling of a clinical symptom indicative of diabetes. Such forestalling includes, for example, the maintenance of normal levels of blood glucose in a subject at risk of developing diabetes prior to the development of overt symptoms of the disease or prior to diagnosis of the disease. Therefore, the term "preventing" includes the prophylactic treatment of subjects to guard them from the occurrence of diabetes. Preventing diabetes in a subject is also intended to include inhibiting or arresting the development of the disease. Inhibiting or arresting the development of the disease includes, for example, inhibiting or arresting the occurrence of abnormal glucose metabolism such as the failure to transfer glucose from the plasma into the cells. Therefore, effective prevention of diabetes would include maintenance of glucose homeostasis due to glucose-regulated insulin expression in an individual predisposed to a diabetic condition, for example, an obese subject or a subject with a family history of diabetes. Inhibiting or arresting the development of the disease also includes, for example, inhibiting or arresting the progression of one or more pathological conditions or chronic complications associated with diabetes.

By "subject" we mean mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

By "at risk" for Type 1 diabetes we mean a) subjects having a blood relative with Type 1 diabetes; b) autoantibody-positive subjects without overt Type 1 diabetes (including cytoplasmic islet cell autoantibodies, insulin antibodies and glutamic acid decarboxylase autoantibodies); c) subjects with Histocompatibility (HLA) type DR3, DQ, or DR4DQW8; and/or d) individuals with glucose abnormalities such as a loss of first phase insulin secretion on glucose tolerance tests. The appearance of at least two antibodies to insulin or a related protein in the blood is generally considered to be predictive of Type 1 diabetes. For instance, there is an 80% incidence of Type 1 diabetes in patients who have at least 2 or 3 of these antibodies. These antibodies signal the beginning of insulitis (inflammation of the islet cells). The antibodies may also signal invasion by cells that destroy the islets.

By "Type 1 diabetes" we mean diabetes characterized as a fasting level of blood glucose greater than or equal to about 140 mg/dl or as a plasma glucose level greater than or equal to about 200 mg/dl as assessed at about 2 hours following the oral administration of a glucose load of about 75 g. The term "diabetes" is also intended to include those subjects with hyperglycemia, including chronic hyperglycemia and impaired glucose tolerance. Plasma glucose levels in hyperglycemic subjects include, for example, glucose concentrations greater than normal as determined by reliable diagnostic indicators. Such hyperglycemic subjects are at risk or predisposed to developing overt clinical symptoms of diabetes mellitus.

By "administering" we mean any means for introducing a compound into the body, preferably into the systemic circulation, as described in more detail below. Examples include but are not limited to oral, buccal, sublingual, pulmonary, transdermal, transmucosal, as well as subcutaneous, intraperitoneal, intravenous, and intramuscular injection.

By "therapeutically effective" we mean an amount of a compound that, when administered to a subject for treating a disease, is sufficient to effect such treatment for the disease. The "therapeutically effective amount" will vary depending on the compound, the disease state being treated, the severity or the disease treated, the age and relative health of the subject, the route and form of administration, the judgment of the attending medical or veterinary practitioner, and other factors.

Dosage.

In one embodiment, the 2AMD and 2MD compounds are individually the active pharmaceutical ingredients (API) of this invention. The API may be formulated in an oral pharmaceutical dosage form as a solution in innocuous solvents, emulsion, suspension or dispersion in suitable solvents or carriers. The API may also be formulated in various oral dosage forms, such as pills, tablets or capsules using suitable pharmaceutical solid carriers. Such pharmaceutical formulations may also contain other pharmaceutically suitable USP-approved inactive ingredients, excipients, such as stabilizers, anti-oxidants, binders, coloring agents, emulsifiers, and/or taste-modifying agents, which are referred to as USP approved inactive pharmaceutical ingredients.

The API may be administered orally, topically, parenterally or transdermally or by inhalation. The compound may be administered by injection or intravenous infusion using suitable sterile solutions. Topical dosage forms may be creams, ointments, patches, or similar vehicles suitable for transdermal and topical dosage forms.

Doses in the range of 0.5 µg to 10 µg per day of the API may be used for the prevention or treatment of Type 1 diabetes according to the present invention. In one embodiment, 2AMD is administered to the subject in doses ranging from 100 pg to 500 pg per kilogram body weight. In other embodiments, 2AMD is administered to the subject in doses ranging from 200-300 pg/kg body weight. In other embodiments, 2MD is administered to the subject in doses ranging from about 0.1-5 ng/kg bodyweight, while in other embodiments, 2MD is administered in doses ranging from about 0.3-0.7 ng/kg bodyweight or 0.5 ng/kg bodyweight. Such doses and dosing regimens may be adjusted to accommodate disease severity or progression, patient predisposition/at-risk/susceptible-to and other known criteria.

The pharmaceutically suitable oral carrier systems (also referred to as drug delivery systems, which are modern technology, distributed with or as a part of a drug product that allows for the uniform release or targeting of drugs to the body) preferably include FDA-approved and/or USP-approved inactive ingredients. Under 21 CFR 210.3(b)(8), an inactive ingredient is any component of a drug product other than the active ingredient. According to 21 CFR 210.3(b)(7), an active ingredient is any component of a drug product intended to furnish pharmacological activity or other direct effect in the diagnosis, cure, mitigation, treatment, or prevention of disease, or to affect the structure or any function of the body of humans or other animals. Active ingredients include those components of the product that may undergo chemical change during the manufacture of the drug product and be present in the drug product in a modified form intended to furnish the specified activity or effect. As used herein, a kit (also referred to as a dosage form) is a packaged collection of related material.

Administration.

As used herein, the oral dosage form includes capsules, a solid oral dosage form consisting of a shell and a filling, whereby the shell is composed of a single sealed enclosure, or two halves that fit together and which are sometimes sealed with a band, and whereby capsule shells may be made from gelatin, starch, or cellulose, or other suitable materials, may be soft or hard, and are filled with solid or liquid ingredients that can be poured or squeezed. The oral dosage form may also be a capsule or coated pellets, in which the drug is enclosed within either a hard or soft soluble container or "shell" made from a suitable form of gelatin. The drug itself may be in the form of granules to which varying amounts of coating have been applied or in a capsule coated extended release, in which the drug is enclosed within either a hard or soft soluble container or "shell" made from a suitable form of gelatin. Additionally, the capsule may be covered in a designated coating which releases a drug or drugs in such a manner to allow at least a reduction in dosing frequency as compared to that drug or drugs presented as a conventional dosage form.

The oral dosage form may further be a capsule delayed release, in which the drug is enclosed within either a hard or soft soluble container made from a suitable form of gelatin, and which releases a drug (or drugs) at a time other than promptly after administration, whereby enteric-coated articles are delayed release dosage forms. Capsule delayed release pellets, in which the drug is enclosed within either a hard or soft soluble container or "shell" made from a are also useful. In these cases, the drug itself is in the form of granules to which enteric coating has been applied, thus delaying release of the drug until its passage into the intestines. Capsule extended release and capsule film-coated extended release are also useful.

Additionally, the capsule is covered in a designated film coating, and which releases a drug or drugs in such a manner to allow at least a reduction in dosing frequency as compared to that drug or drugs presented as a conventional dosage form), capsule gelatin coated (a solid dosage form in which the drug is enclosed within either a hard or soft soluble container made from a suitable form of gelatin; through a banding process, the capsule is coated with additional layers of gelatin so as to form a complete seal), capsule liquid filled (a solid dosage form in which the drug is enclosed within a soluble, gelatin shell which is plasticized by the addition of a polyol, such as sorbitol or glycerin, and is therefore of a somewhat thicker consistency than that of a hard shell capsule.

Typically, the active ingredients are dissolved or suspended in a liquid vehicle), granule (a small particle or grain), pellet (a small sterile solid mass consisting of a highly purified drug, with or without excipients, made by the formation of granules, or by compression and molding), pellets coated extended release (a solid dosage form in which the drug itself is in the form of granules to which varying amounts of coating have been applied, and which releases a drug or drugs in such a manner to allow a reduction in dosing frequency as compared to that drug or drugs presented as a conventional dosage form).

Other forms include pills (a small, round solid dosage form containing a medicinal agent intended for oral administration), powder (an intimate mixture of dry, finely divided drugs and/or chemicals that may be intended for internal or external use), elixir (a clear, pleasantly flavored, sweetened hydroalcoholic liquid containing dissolved medicinal agents; it is intended for oral use), chewing gum (a sweetened and flavored insoluble plastic material of various shapes which when chewed, releases a drug substance into the oral cavity), syrup (an oral solution containing high concentrations of sucrose or other sugars; the term has also been used to include any other liquid dosage form prepared in a sweet and viscid vehicle, including oral suspensions), tablet (a solid dosage form containing medicinal substances with or without suitable diluents), tablet chewable (a solid dosage form containing medicinal substances with or without suitable diluents that is intended to be chewed, producing a pleasant tasting residue in the oral cavity that is easily swallowed and does not leave a bitter or unpleasant after-taste), tablet coated or tablet delayed release, tablet dispersible, tablet effervescent, tablet extended release, tablet film coated, or tablet film coated extended release where the tablet is formulated in such manner as to make the contained medicament available over an extended period of time following ingestion.

In other forms, a tablet for solution, tablet for suspension, tablet multilayer, tablet multilayer extended release may be provided, where the tablet is formulated in such manner as to allow at least a reduction in dosing frequency as compared to that drug presented as a conventional dosage form. A tablet orally disintegrating, tablet orally disintegrating delayed release, tablet soluble, tablet sugar coated, osmotic, and the like are also suitable.

The oral dosage form composition contains an active pharmaceutical ingredient and one or more inactive pharmaceutical ingredients such as diluents, solubilizers, alcohols, binders, controlled release polymers, enteric polymers, disintegrants, excipients, colorants, flavorants, sweeteners, antioxidants, preservatives, pigments, additives, fillers, suspension agents, surfactants (e.g., anionic, cationic, amphoteric and nonionic), and the like. Various FDA-approved topical inactive ingredients are found at the FDA's "The Inactive Ingredients Database" that contains inactive ingredients specifically intended as such by the manufacturer, whereby inactive ingredients can also be considered active ingredients under certain circumstances, according to the definition of an active ingredient given in 21 CFR 210.3(b)(7). Alcohol is a good example of an ingredient that may be considered either active or inactive depending on the product formulation.

As used herein, the injectable and infusion dosage forms include, but are not limited to, a liposomal injectable, which either consists of or forms liposomes (a lipid bilayer vesicle usually composed of phospholipids which is used to encapsulate an active drug substance). An injection, which includes a sterile preparation intended for parenteral use; five distinct classes of injections exist as defined by the USP, is also suitable. An emulsion injection, which includes an emulsion consisting of a sterile, pyrogen-free preparation intended to be administered parenterally or a lipid complex injection are also suitable.

Other forms include a powder for solution injection, which is a sterile preparation intended for reconstitution to form a solution for parenteral use; a powder for suspension injection that is a sterile preparation intended for reconstitution to form a suspension for parenteral use; a powder lyophilized for liposomal suspension injection, which is a sterile freeze dried preparation intended for reconstitution for parenteral use which has been formulated in a manner that would allow liposomes (a lipid bilayer vesicle usually composed of phospholipids which is used to encapsulate an active drug substance, either within a lipid bilayer or in an aqueous space) to be formed upon reconstitution; a powder lyophilized for solution injection, which is a dosage form intended for the solution prepared by lyophilization ("freeze drying"), a process which involves the removal of water from products in the frozen state at extremely low pressures.

This is intended for subsequent addition of liquid to create a solution that conforms in all respects to the requirements for injections; a powder lyophilized for suspension injection being a liquid preparation, intended for parenteral use that contains solids suspended in a suitable fluid medium and conforms in all respects to the requirements for Sterile Suspensions; the medicinal agents intended for the suspension are prepared by lyophilization ("freeze drying"), a process which involves the removal of water from products in the frozen state at extremely low pressures; a solution injection being a liquid preparation containing one or more drug substances dissolved in a suitable solvent or mixture of mutually miscible solvents that is suitable for injection; a solution concentrate injection being a sterile preparation for parenteral use which, upon the addition of suitable solvents, yields a solution conforming in all respects to the requirements for injections.

A suspension injection comprises a liquid preparation, suitable for injection, which consists of solid particles dispersed throughout a liquid phase in which the particles are not soluble that can also consist of an oil phase dispersed throughout an aqueous phase, or vice-versa. A suspension liposomal injection comprises a liquid preparation, suitable for injection, which consists of an oil phase dispersed throughout an aqueous phase in such a manner that liposomes (a lipid bilayer vesicle usually composed of phospholipids which is used to encapsulate an active drug substance, either within a lipid bilayer or in an aqueous space) are formed. A suspension sonicated injection comprises a liquid preparation, suitable for injection, which consists of solid particles dispersed throughout a liquid phase in which the particles are not soluble. In addition, the product is sonicated while a gas is bubbled through the suspension, and this results in the formation of microspheres by the solid particles.

The parenteral carrier system includes one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives. Formulations suitable for parenteral administration conveniently comprise a sterile oily or aqueous preparation of the active ingredient which is preferably isotonic with the blood of the recipient.

As used herein, inhalation dosage forms include, but are not limited to, aerosol being a product that is packaged under pressure and contains therapeutically active ingredients that are released upon activation of an appropriate valve system intended for topical application to the skin as well as local application into the nose (nasal aerosols), mouth (lingual and sublingual aerosols), or lungs (inhalation aerosols); foam aerosol being a dosage form containing one or more active ingredients, surfactants, aqueous or nonaqueous liquids, and the propellants, whereby if the propellant is in the internal (discontinuous) phase (i.e., of the oil-in-water type), a stable foam is discharged, and if the propellant is in the external (continuous) phase (i.e., of the water-in-oil type), a spray or a quick-breaking foam is discharged; metered aerosol being a pressurized dosage form consisting of metered dose valves which allow for the delivery of a uniform quantity of spray upon each activation; powder aerosol being a product that is packaged under pressure and contains therapeutically active ingredients, in the form of a powder, that are released upon activation of an appropriate valve system; and, aerosol spray being an aerosol product which utilizes a compressed gas as the propellant to provide the force necessary to expel the product as a wet spray and being applicable to solutions of medicinal agents in aqueous solvents.

As used herein, transdermal dosage form includes, but is not limited to, a patch being a drug delivery system that often contains an adhesive backing that is usually applied to an external site on the body, whereby the ingredients either passively diffuse from, or are actively transported from, some portion of the patch, and whereby depending upon the patch, the ingredients are either delivered to the outer surface of the body or into the body; and, other various types of transdermal patches such as matrix, reservoir and others known in the art.

As used herein, the topical dosage form includes various dosage forms known in the art such as lotions (an emulsion, liquid dosage form, whereby this dosage form is generally for external application to the skin), lotion augmented (a lotion dosage form that enhances drug delivery, whereby augmentation does not refer to the strength of the drug in the dosage form), gels (a semisolid dosage form that contains a gelling agent to provide stiffness to a solution or a colloidal dispersion, whereby the gel may contain suspended particles) and ointments (a semisolid dosage form, usually containing <20% water and volatiles and >50% hydrocarbons, waxes, or polyols as the vehicle, whereby this dosage form is generally for external application to the skin or mucous membranes).

Ointment augmented (an ointment dosage form that enhances drug delivery, whereby augmentation does not refer to the strength of the drug in the dosage form), creams (an emulsion, semisolid dosage form, usually containing >20% water and volatiles and/or <50% hydrocarbons, waxes, or polyols may also be used as the vehicle, whereby this dosage form is generally for external application to the skin or mucous membranes. Cream augmented (a cream dosage form that enhances drug delivery, whereby augmentation does not refer to the strength of the drug in the dosage form), emulsions (a dosage form consisting of a two-phase system comprised of at least two immiscible liquids, one of which is dispersed as droplets, internal or dispersed phase, within the other liquid, external or continuous phase, generally stabilized with one or more emulsifying agents, whereby emulsion is used as a dosage form term unless a more specific term is applicable, e.g. cream, lotion, ointment), suspensions (a liquid dosage form that contains solid particles dispersed in a liquid vehicle), suspension extended release, pastes (a semisolid dosage form, containing a large proportion, 20-50%, of solids finely dispersed in a fatty vehicle, whereby this dosage form is generally for external application to the skin or mucous membranes), solutions (a clear, homogeneous liquid dosage form that contains one or more chemical substances dissolved in a solvent or mixture of mutually miscible solvents), and powders are also suitable.

Shampoos (a lotion dosage form which has a soap or detergent that is usually used to clean the hair and scalp) are often used as a vehicle for dermatologic agents. For instance, shampoo suspensions (a liquid soap or detergent containing one or more solid, insoluble substances dispersed in a liquid vehicle that is used to clean the hair and scalp and is often used as a vehicle for dermatologic agents) are often used. Aerosol foams (i.e., a dosage form containing one or more active ingredients, surfactants, aqueous or nonaqueous liquids, and the propellants; if the propellant is in the internal discontinuous phase, i.e., of the oil-in-water type, a stable foam is discharged, and if the propellant is in the external continuous phase, i.e., of the water-in-oil type, a spray or a quick-breaking foam is discharged), sprays (a liquid minutely divided as by a jet of air or steam), metered spray (a non-pressurized dosage form consisting of valves which allow the dispensing of a specified quantity of spray upon each activation), and suspension spray (a liquid preparation containing solid particles dispersed in a liquid vehicle and in the form of coarse droplets or as finely divided solids to be applied locally, most usually to the nasal-pharyngeal tract, or topically to the skin) are also suitable.

Jellies (a class of gels, which are semisolid systems that consist of suspensions made up of either small inorganic particles or large organic molecules interpenetrated by a liquid—in which the structural coherent matrix contains a high portion of liquid, usually water) and films (a thin layer or coating), including film extended release (a drug delivery system in the form of a film that releases the drug over an extended period in such a way as to maintain constant drug levels in the blood or target tissue) and film soluble (a thin layer or coating which is susceptible to being dissolved when in contact with a liquid) are also suitable.

Sponges (a porous, interlacing, absorbent material that contains a drug, whereby it is typically used for applying or introducing medication, or for cleansing, and whereby a sponge usually retains its shape), swabs (a small piece of relatively flat absorbent material that contains a drug, whereby a swab may also be attached to one end of a small stick, and whereby a swab is typically used for applying medication or for cleansing).

Patches (a drug delivery system that often contains an adhesive backing that is usually applied to an external site on the body, whereby its ingredients either passively diffuse from, or are actively transported from, some portion of the patch, whereby depending upon the patch, the ingredients are either delivered to the outer surface of the body or into the body, and whereby a patch is sometimes synonymous with the terms 'extended release film' and 'system'), patch extended release (a drug delivery system in the form of a patch that releases the drug in such a manner that a reduction in dosing frequency compared to that drug presented as a conventional dosage form, e.g., a solution or a prompt drug-releasing, conventional solid dosage form), patch extended release electronically controlled (a drug delivery system in the form of a patch which is controlled by an electric current that releases the drug in such a manner that a reduction in dosing frequency compared to that drug presented as a conventional dosage form, e.g., a solution or a prompt drug-releasing, conventional solid dosage form), and the like. The various topical dosage forms may also be formulated as immediate release, controlled release, sustained release, or the like.

The topical dosage form composition contains an active pharmaceutical ingredient and one or more inactive pharmaceutical ingredients such as excipients, colorants, pigments, additives, fillers, emollients, surfactants (e.g., anionic, cationic, amphoteric and nonionic), penetration enhancers (e.g., alcohols, fatty alcohols, fatty acids, fatty acid esters and polyols), and the like. Various FDA-approved topical inactive ingredients are found at the FDA's "The Inactive Ingredients Database" that contains inactive ingredients specifically intended as such by the manufacturer, whereby inactive ingredients can also be considered active ingredients under certain circumstances, according to the definition of an active ingredient given in 21 CFR 210.3(b)(7). Alcohol is a good example of an ingredient that may be considered either active or inactive depending on the product formulation.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description of the novel methods of the present invention are to be regarded as illustrative in nature and not restrictive.

EXAMPLES

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

Example 1

2AMD Type 1 Diabetes Prevention Study

In this example, the inventors show the effect of 2AMD on preventing NOD mice from developing Type 1 diabetes.

Diet. Breeding pairs were fed LabDiet™ Mouse Diet 5010 ad libitum (PMI Nutrition International, St. Louis, Mo.). Experimental mice were fed LabDiet™ Mouse Diet 5K52 meal form (PMI Nutrition International, St. Louis, Mo.). Female pups were weaned at three weeks and placed immediately on the 5010 diet. At eight weeks of age, mice were placed on 1 of 4 experimental diets: 1) chow, 2) 5010+50 ng 1,25(OH)$_2$D$_3$, or 3) 5010+200 pg and 4) 5010+300 pg 2AMD. In diets/treatments containing 1,25(OH)$_2$D$_3$ or 2AMD, the hormone was added to 1% Wesson® oil and mixed into the diet. Diets were fed in food cups at 3.5 g food/mouse/day and were replaced 3 times per week.

Evaluation of Diabetic Status. All experimental mice were weighed weekly and urinalysis was performed weekly starting at 10 weeks of age—Diastix® (Bayer, Elkhart, Ind.) were used to determine glucose levels. If a Diastix® reading was above 1000 mg/dl, the mice were bled from maxillary cheek following a 4 hour fast. Whole blood was centrifuged to obtain serum. Concentration of glucose in serum was measured using a enzymatic-colorimetric assay (Glucose Liquicolor®, Stanbio Laboratory, Boerne, Tex.) followed by spectrophotometric analysis. Animals that had two fasting glucose analysis above 300 mg/dl were diagnosed as diabetic and sacrificed via CO$_2$ asphyxiation.

Serum Calcium Analysis. Blood was collected from maxillary cheek of each mouse weekly from 8 weeks to 200 days of age. Serum was separated by centrifugation and diluted 1:40 in a 0.1% LaCl$_2$ solution. Calcium concentration was determined by atomic absorption spectrometry (Spectrometer 3110®, Perkin Elmer, Norwalk, Conn.).

Results. Type 1 Diabetes incidence in the 5010 group was 64% (7/11). NOD mice fed 50 ng 1,25(OH)$_2$D$_3$ in the 5010 diet per day were completely protected against T1DM. However, serum calcium values were elevated at 12 mg/dl. NOD mice fed two dosages of 200 pg and 300 pg of 2AMD resulted in disease incidence of 8% (1/12) without hypercalcemia. Weight was not altered by 2AMD, while 1,25(OH)$_2$D$_3$ diminished weight of the mouse (probably because of hypercalcemia).

Example 2

2MD Type 1 Diabetes Prevention Study

In this example, the inventors show the effect of 2MD on preventing NOD mice from developing Type 1 diabetes.

Diet. Breeding pairs were maintained on LabDiet Mouse Diet 5015 (PMI Nutrition International, St. Louis, Mo.) containing 0.8% calcium and 3.3 IU vitamin D$_3$/g diet. Female pups were weaned at three weeks and placed immediately on a purified diet (Suda et al., 1974, *J. Nutr.* 100: 1049-1052). At eight weeks of age, mice were then provided 1 of 4 experimental diets: diet 11 only or diet 11+50 ng 1,25(OH)$_2$D$_3$, diet 11 plus 400 ng 2MP or diet 11+500 pg 2MD. All purified diets were supplemented with vegetable oil containing fat soluble vitamins A, E, D and K (Suda et al., 1970, *J. Nutr.* 100: 1049-1052 [diet 11]). In diets containing 1,25(OH)$_2$D$_3$, 2MP or 2MD, the compounds were added to 1% Wesson® oil and mixed into the purified diet. Diets were fed in agar form (Hayes et al., 1987, *J. Nutr.* 117:857-865) at 3.5 g food/mouse/day and were replaced three times per week.

Evaluation of Diabetic Status. All experimental mice were weighed weekly and urinalysis was performed weekly starting at 10 weeks of age—Diastix® (Bayer, Elkhart, Ind.) were used to determine glucose levels. If a Diastix® reading was above 1000 mg/dl, the mice were bled from maxillary cheek following a four-hour fast. Whole blood was centrifuged to obtain serum. Concentration of glucose in serum was measured using a enzymatic-colorimetric assay (Glucose Liquicolor®, Stanbio Laboratory, Boerne, Tex.) followed by spectrophotometric analysis. Animals that had two fasting glucose analysis above 300 mg/dl were diagnosed as diabetic and sacrificed via CO$_2$ asphyxiation.

Serum Calcium Analysis. Blood was collected from maxillary cheek of each mouse at 6, 8, 9, 14.3, 15.3 and 28.6 weeks of age. Serum was separated by centrifugation and diluted 1:40 in a 0.1% LaCl$_2$ solution. Calcium concentration was determined by atomic absorption spectrometry (Spectrometer 3110®, Perkin Elmer, Norwalk, Conn.).

Results. As expected, control NOD mice receiving diet 11 showed a 30% incidence of diabetes. Even at 400 ng, 2MP afforded no protection against diabetes, while 50 ng/day 1,25 (OH)$_2$D$_3$ and 0.5 ng/day 2MD (FIG. 4) prevented diabetes. All animals grew equally well irrespective of the specific vitamin D compounds. Hypercalcemia was found in the mice given 1,25(OH)$_2$D$_3$, while a moderate elevation of calcium was found in those given 0.5 ng 2MD and 400 ng 2MP (Table 2 and FIG. 6).

TABLE 1

Incidence of Type 1 Diabetes.

| Treatment | Incidence |
|---|---|
| Diet 11 (n = 24) | 29.2% |
| 50 ng 1.25 (n = 24) | 4.2% |
| 400 ng 2MP (n = 12) | 33.0% |
| 0.5 ng 2MD (n = 12) | 0.0 |

TABLE 2

Serum Calcium Levels.

| Age (Weeks) | Group 1 Purified | Group 2 50 ng 1.25 | Group 8 0.5 ng 2MD | Group 10 400 ng 2MP | Age (Weeks) | Group 1 Purified | Group 2 50 ng 1.25 | Group 8 0.5 ng 2MD | Group 10 400 ng 2MP |
|---|---|---|---|---|---|---|---|---|---|
| | Weights | | | | | Calcium | | | |
| 3 | 12.92 | 12.46 | 13.33 | 13.60 | 6 | 9.80 | 12.15 | 11.42 | 11.57 |
| 6 | 21.75 | 20.46 | 21.87 | 22.03 | 8 | 9.58 | 12.32 | 11.45 | 11.57 |

TABLE 2-continued

Serum Calcium Levels.

| | | | | | | | | |
|---|---|---|---|---|---|---|---|---|
| 8 | 23.20 | 22.52 | 23.78 | 23.74 | 9 | 9.38 | 12.67 | 11.55 | 11.55 |
| 9 | 24.10 | 23.63 | 24.94 | 24.63 | 14.3 | 9.52 | 12.82 | 11.52 | 11.62 |
| 14.3 | 27.28 | 25.02 | 27.85 | 26.30 | 15.3 | 9.80 | 12.35 | 11.33 | 11.77 |
| 15.3 | 27.55 | 25.06 | 27.82 | 26.81 | 28.6 | 9.58 | 12.75 | 11.37 | 11.66 |
| 28.6 | 30.39 | 25.85 | 29.51 | 27.64 | | | | | |

| Std dev (weight) | | | | | Std dev (calcium) | | | |
|---|---|---|---|---|---|---|---|---|
| 3 | 1.96 | 1.72 | 2.11 | 2.22 | 3 | na | na | na | na |
| 6 | 2.15 | 1.27 | 1.40 | 2.20 | 6 | 0.36 | 0.53 | 0.40 | 0.39 |
| 8 | 2.68 | 1.62 | 1.74 | 2.15 | 8 | 0.23 | 0.81 | 0.45 | 0.65 |
| 9 | 2.56 | 1.97 | 2.01 | 2.10 | 9 | 0.52 | 0.76 | 0.44 | 0.48 |
| 14.3 | 2.46 | 2.19 | 1.92 | 2.12 | 14.3 | 1.01 | 0.96 | 0.38 | 0.62 |
| 15.3 | 2.40 | 2.17 | 2.20 | 1.85 | 15.3 | 0.23 | 1.73 | 0.36 | 0.58 |
| 28.6 | 3.28 | 1.97 | 2.81 | 1.96 | 28.6 | 0.27 | 0.77 | 0.45 | 0.34 |

| SEM (weight) | | | | | SEM (calcium) | | | |
|---|---|---|---|---|---|---|---|---|
| 3 | 0.565 | 0.497 | 0.609 | 0.641 | 6 | 0.104 | 0.152 | 0.114 | 0.113 |
| 6 | 0.620 | 0.367 | 0.405 | 0.635 | 8 | 0.067 | 0.234 | 0.131 | 0.188 |
| 8 | 0.774 | 0.468 | 0.502 | 0.621 | 9 | 0.150 | 0.221 | 0.126 | 0.139 |
| 9 | 0.740 | 0.567 | 0.580 | 0.607 | 14.3 | 0.292 | 0.276 | 0.109 | 0.179 |
| 14.3 | 0.710 | 0.633 | 0.554 | 0.611 | 15.3 | 0.065 | 0.499 | 0.102 | 0.167 |
| 15.3 | 0.692 | 0.626 | 0.634 | 0.533 | 28.6 | 0.078 | 0.222 | 0.130 | 0.098 |
| 28.6 | 0.947 | 0.569 | 0.810 | 0.566 | | | | | | n = 12 for all groups

It should be noted that the above description, attached figures and their descriptions are intended to be illustrative and not limiting of this invention. Many themes and variations of this invention will be suggested to one skilled in this and, in light of the disclosure. All such themes and variations are within the contemplation hereof. For instance, while this invention has been described in conjunction with the various exemplary embodiments outlined above, various alternatives, modifications, variations, improvements, and/or substantial equivalents, whether known or that rare or may be presently unforeseen, may become apparent to those having at least ordinary skill in the art. Various changes may be made without departing from the spirit and scope of the invention. Therefore, the invention is intended to embrace all known or later-developed alternatives, modifications, variations, improvements, and/or substantial equivalents of these exemplary embodiments.

We claim:

1. A method of preventing Type 1 diabetes in a subject at risk of developing Type 1 diabetes, the method comprising administering to the subject a therapeutically effective amount of 2α-methyl-19-nor-20(S)-1α,25-dihydroxyvitamin $D_3$, wherein Type 1 diabetes is prevented from developing in the subject without inducing hypercalcemia in the subject.

2. The method of claim 1, wherein the 2α-methyl-19-nor-20(S)-1α,25-dihydroxyvitamin $D_3$ is formulated in an oral, topical, transdermal, parenteral, injection or infusion dosage form.

3. The method of claim 1, wherein the therapeutically effective amount comprises ranges from about 50 ng/day to about 500 ng/day.

4. A method of preventing Type 1 diabetes in a subject at risk of developing Type 1 diabetes, the method comprising administering to the subject a therapeutically effective amount of 2-methylene-19-nor-20(S)-1,25-dihydroxyvitamin $D_3$, wherein Type 1 diabetes is prevented from developing in the subject without inducing hypercalcemia in the subject.

5. The method of claim 4, wherein the 2-methylene-19-nor-20(S)-1,25-dihydroxyvitamin $D_3$ is formulated in an oral, topical, transdermal, parenteral, injection or infusion dosage form.

6. The method of claim 4, wherein the therapeutically effective amount ranges from about 50 ng/day to about 500 ng/day.

* * * * *

UNITED STATES PATENT AND TRADEMARK OFFICE
CERTIFICATE OF CORRECTION

PATENT NO. : 8,349,818 B2
APPLICATION NO. : 12/909253
DATED : January 8, 2013
INVENTOR(S) : DeLuca et al.

It is certified that error appears in the above-identified patent and that said Letters Patent is hereby corrected as shown below:

In the Specification:

Column 2, Line 45 "16895-16965" should read -- 1689S-1696S --

Signed and Sealed this
Eleventh Day of June, 2013

Teresa Stanek Rea
*Acting Director of the United States Patent and Trademark Office*